United States Patent [19]

Davydov et al.

[11] 4,035,334
[45] July 12, 1977

[54] MEDICAL ADHESIVE

[76] Inventors: Anatoly Borisovich Davydov, ulitsa Krasny Kazanets, 19, korpus 1, kv. 283; Alla Yakovlevna Akimova, ulitsa Kosmonavta Volkova, 1, kv. 155; Vasily Vladimirovich Korshak, ulitsa Gubkina, 4, kv. 84, all of Moscow; Nikolai Nikolaevich Trofimov, Bulvar Zhdanova, 33/22, kv. 38; Volf Samoilovich Etlis, Prospekt Lenina, 59, kv. 56, both of Dzerzhinsk Gorkovskoi oblasti; Alexandr Alexandrovich Vishnevsky, Novokuznetskaya ulitsa, 13/15, kv. 269; Vitaly Rafailovich Belkin, Smolensky bulvar, 15, kv. 100, both of Moscow, all of U.S.S.R.

[21] Appl. No.: 683,941

[22] Filed: May 6, 1976

Related U.S. Application Data

[63] Continuation-in-part of Ser. No. 305,587, Nov. 11, 1972, abandoned.

[51] Int. Cl.$^2$ .......................................... C08K 5/04
[52] U.S. Cl. ............................. 260/42.21; 128/82; 128/334 R; 260/378; 260/881; 424/81
[58] Field of Search ............... 260/42.21, 881, 378

[56] References Cited

U.S. PATENT DOCUMENTS

| 2,459,149 | 1/1949 | Coover et al. | 260/378 |
| 3,178,379 | 4/1965 | Wicker et al. | 260/881 |

*Primary Examiner*—James H. Derrington

[57] ABSTRACT

Medical adhesive composition comprising the following components in preferably the indicated percents by weight:

2-ethoxyethyl-α-cyanoacrylate . . . 84.9–96.98
polyvinyl-n-butyl ether having the general formula,

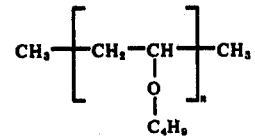

wherein $n$ is a number sufficient to provide a molecular weight of about 4,000 to 10,000 . . . 3–15
and as a fat-soluble, green stain or dye, 1,4-bis-(p-toluidino)-anthraquinone having the formula,

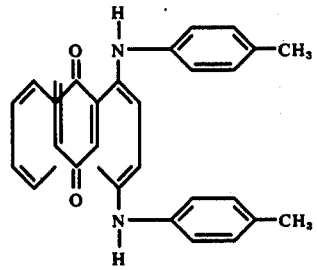

0.02–0.1

The adhesive is useful for joining soft tissues in surgical operations.

3 Claims, No Drawings

MEDICAL ADHESIVE

BACKGROUND OF THE INVENTION

This application is a continuation-in-part of our co-pending application U.S. Ser. No. 305,587, filed Nov. 11, 1972 now abandoned and entitled "Medical Glue."

This invention relates to a new medical adhesive composition. More particularly, the invention relates to an improved medical adhesive composition comprising 2-ethoxyethyl-α-cyanoacrylate, polyvinyl-n-butyl ether having a molecular weight of 4,000 to 10,000 and as a fat-soluble green anthraquinone stain or dye, 1,4-bis-(p-toluidino)-anthraquinone.

Adhesives consisting of α-cyanoacrylate and mixtures thereof with various thickeners, such as unsaturated acid esters, for example polybutylmethacrylate, polymethylmethacrylate, polyethylmethacrylate and also which contain anthraquinone dyes, the distinctive feature of which is the presence of a functional amide group

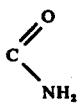

and which contain, as well, a plasticizer, such as aryl and diaryl monomeric ethers are known. (U.S. Pat. Nos. 2,784,215; 3,699,127; 3,361,765).

However, these known adhesives have a number of disadvantages which limit their application in the field of medicine. For example, application of an adhesive consisting of α cyanoacrylate to the surface of an object generally results in the formation of a rigid and brittle film. Such a film does not effect the joining of living tissues and, moreover causes additional traumatization.

An adhesive comprising aryl or diaryl monomeric ether as a plasticizer is likewise not suitable for use in medicine due to the high toxicity of such a plasticizer. Adhesives comprising thickeners, such as unsaturated acid esters like polybutylmethacrylate, polymethylmethacrylate and polyethylmethacrylate form dense adhesive films, which prevent regeneration of joined tissues when applied in the medical field.

Moreover, where an anthraquinone dye comprising an amide group is employed as an adhesive component, it generally affects the stability of the properties of such an adhesive during storage.

There is also known a medical adhesive which comprises by weight 80 to 92 percent of ethyl-α-cyanoacrylate and 8 to 20 percent of polyvinyl acetate having a molecular weight of 15,000 to 20,000.

This adhesive is prepared by dissolving polyvinyl acetate in ethyl chloride and adding ethylcyanoacrylate to the solution. Ethyl chloride is then removed by disposing the mixture over phosphorus pentoxide.

The disadvantage of the described medical adhesive is the brittleness of the film that is produced by the adhesive when it sets. This is caused primarily by the ethylcyanoacrylate used as the basic component in the adhesive and also to the impossibility of application of the adhesive onto the surface of a wound by spraying because of the quick polymerization of the adhesive when it is in a finely dispersed state.

Moreover, owing to the absence of pigment in the adhesive, it is difficult to control the process of its application and to identify it on the tissues. In some cases, such as in ophthalmology and neurosurgery, the strength of the cemented joint is insufficient. This limits the field of application of the adhesive.

Consequently, in view of the numerous drawbacks of the known adhesives described above, especially in their application to the medical field, there exists a need for an adhesive which can be employed in the field of medicine which does not present such disadvantages. The present invention fulfills this needs.

THE OBJECTS OF THE INVENTION

It is, therefore, a primary object of this invention to provide a medical adhesive which forms a film which exhibits sufficient strength and elasticity on setting and which also is capable of promoting wounnd healing.

Another object of the invention is to provide an adhesive that is easy to control during application and that can be applied in an even layer.

BRIEF STATEMENT OF THE INVENTION

In accordance with this invention, the above objects are attained by providing a medical adhesive composition comprising by weight a major proportion of 2-ethoxyethyl-α-cyanoacrylate, and minor proportions of polyvinyl-n-butyl ether having a molecular weight of about 4,000 to 10,000 and as a fat-soluble green stain or dye, 1,4-bis-(p-toluidino)-anthraquinone, the components totaling 100 percent and the acrylate being employed preferably in a range of 84.9 to 98.98 percent, the ether preferably in a range of 3 to 15 percent and the stain or dye preferably in a range of 0.02 to 0.1 percent.

DESCRIPTION OF THE PREFERRED EMBODIMENTS

More specifically a medical adhesive composition in accordance with the present invention comprises preferably the following components in percent by weight:

2-ethoxyethyl-α-cyanoacrylate . . . 84.9–96.98
polyvinyl-n-butyl ether having the general formula,

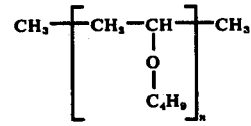

wherein n is a number sufficient to provide a molecular weight of about 4,000 to 10,000, 3–15
and as a fat-soluble, green stain or dye, 1,4-bis-(p-toluidino)- anthraquinone having the formula,

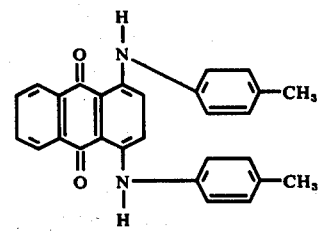

0.03–0.1

A further preferred medical adhesive composition according to the invention comprises in percent by weight 94.15 percent of the acrylate, 5.8 percent of the ether and 0.05 percent of the dye. Moreover, it is to be understood that any polyvinyl-n- butyl ether having the recurring structural group indicated in the formula set forth hereinabove for the ethers and which also has a value for n which is sufficient to provide a molecular weight in the disclosed range can be employed in a medical adhesive according to the present invention. In this regard, it is to be further understood that the molecular weight thereof is determined by the standard light dispersion or reverse ebullioscope method employing n-heptane as a solvent.

The adhesive can be prepared as follows.

The starting components -2-ethoxyethyl-α-cyanoacrylate, suitable polyvinyl-n-butyl ether and suitable fat-soluble green dye are mixed in a dry, noble gaseous medium, such as nitrogen or argon gas and the like in a suitable vessel. If the polyvinylbutyl ether contains volatile admixtures, they are removed by heating to 50°-60° C. at a residual pressure of 1 mm Hg. on initial mixing of the starting components, the vessel is closed tightly and placed on a shaker for 3 hours. The so prepared adhesive is then filled in 1-milliliter portions into 1.5-2 ml polyethylene ampoules and sealed. The adhesive is then to be stored at a temperature from 0° to 4° C. and has a storage term of at least 6 months.

In use the adhesive is applied onto a wound surface directly from the ampoule, which is punctured by a sterile needle, or with various rods, brushes or spatulas made of synthetic polymers. In addition, the adhesive can be applied with other special tools and sprayers.

Before application of the adhesive, surfaces, such as tissue surfaces to be joined, are dried with a gauze pad and, then with a pad soaked in alcohol or ether.

The medical adhesive of this invention was tested clinically on 150 patients. It was used for closing the bed of the gall bladder and for fastening the bile duct stump (in fifteen patients). In these cases, the adhesive was applied directly from the punctured ampoule. No complications were encountered.

In treating penetrating wounds of the eye ball and also for fixing transplants in stepped cornea transplantations (in fifteen patients), the adhesive was applied onto the surfaces to be joined with a polyethylene capillary. No delamination was observed in these cases. The wound healing process was accomplished without any complications.

The adhesive was also tested in operations on the lungs involving tuberculosis to seal ruptures in the pulmonary parenchyma, for extra safety in sealing mechanical sutures and for muscular plasty of the broncheal stump (in eighteen patients).

Special tools and a sprayer were used in these cases, and full tightness of the seams was attained in all of them. The spraying technique was used in closing defects of the renal parenchyma, for additional sealing of the stumps of the main and the lobular bronchi and for eradication of broncheal fistulas (in fifteen patients). No complications were observed in the post-operative period.

The adhesive was tested also in cases involving superficial fastening, such as, in keratoplasty (in ten patients), for fixing layers of keratotransplants in partial stepped transplantation of the cornea and also for cases involving recurrent harpetic keratitis and pterygium (in six patients); it was used for post-operative treatment of the anterior chamber, for correction and incision of the iris and for removal of cataractal mass (in four patients). In these cases, the adhesive was applied with rods and spatulas made of synthetic polymers. No side effects or contraindications were noted. In all cases the wounds healed without complications.

The proposed new adhesive exhibits certain advantages over the known adhesives with respect to its physico-mechanical, physico-chemical and medicobiological properties. The proposed adhesive forms a strong and elastic film on setting during the joining of the live tissues. In the composition of this invention the polyvinyl-n-butyl ethers used are unlike known modified additives employed for the same purpose and are high molecular weight compounds which have no toxic effects on living tissue.

Polyvinyl-n-butyl ethers such as those used herein are known under the name of Balsam of Shostakovsky and are applied as pharmaceuticals according to the USSR pharmacopoeia, Edition X, Clause 732.

The established effect of such a typical polyvinyl-n-butyl ether on elasticity is illustrated in tabular form as follows:

| Temperature C° | Deformation in % | | |
|---|---|---|---|
| | ethoxyethyl-cyanoacrylate | ethoxyethyl-cyanoacrylate +5%-polyvinyl-n-butyl ether | ethoxyethyl-cyanoacrylate +8%-polyvinyl-n-butyl ether |
| 1 | 2 | 3 | 4 |
| 20 | 0 | 0.75 | 0 |
| 25 | 1.35 | 2.15 | 1.51 |
| 37 | 2.7 | 5.71 | 9.05 |
| 45 | 8.8 | 12.1 | 15.06 |
| 50 | 14.2 | 20.0 | 27.3 |
| 60 | 40.5 | 42.9 | 60.5 |
| 70 | 63.5 | 61.5 | 91 |
| 74 | — | — | 100 |
| 80 | 83.8 | 78 | — |

The presence of polyvinylbutyl ether in the adhesive, promotes the healing process. The dark green color of the adhesive makes it easy to control the zone of adhesive application and the local and controlled-dose application of the adhesive makes it possible to apply films of even thickness.

Unlike the known medical adhesives referred to above, the adhesive of this invention can be applied by spraying. Moreover, the polymerized adhesive of this invention can be easily removed from tools, instruments and medical gloves with which it comes into contact with readily available solvents, such as alcohol or acetone. In contrast, the polymerized known medical adhesives can be dissolved completely only in nitromethane and dimethyl sulphoxide.

THE EXAMPLES

For a better understanding of the invention, the following examples are given by way of illustration:

EXAMPLE 1

A medical adhesive having the following composition in percent by weight was prepared.
2-ethoxyethyl-α-cyanoacrylate . . . 94.15
polyvinyl-n-butyl ether having the general formula,

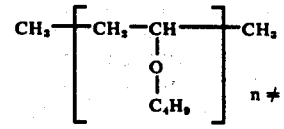

and a mol. wt. of 7000-8000 . . . 5.8 and as fat-soluble anthraquinone green stain or dye, 1,4-bis (p- toluidino)-anthraquinone having the formula,

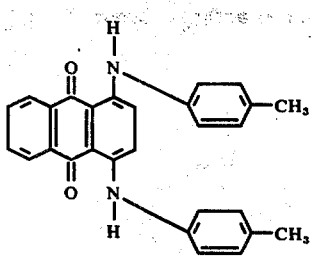

0.05

Before mixing with the other components of the adhesive, the polyvinyl-n-butyl ether and the dye were dried to constant weight at a temperature of 60° C and residual pressure of 1 mm Hg. The components of the adhesive were mixed in an atmosphere of dry argon. Polyvinyl-n-butyl ether and the dye were placed in a glass vessel and 2-ethoxyethyl-α-cyanoacrylate was added. The vessel was closed tightly with a polyethylene stopper, sealed with paraffin and placed on a mechanical shaker. After 4 hours of shaking, a dark green homogeneous mass was formed. The prepared adhesive was filled in 1ml portions into polyethylene ampoules in an atmosphere of dry argon and sealed. The ampoules were put into glass test-tubes filled with indicator silica gel. The test-tubes were sealed hermetically with polyethylene stoppers.

EXAMPLE 2

A medical adhesive having the following composition in percent by weight was prepared.
2-ethoxyethyl-α-cyanoacrylate ... 96.98
polyvinyl-n-butyl ether having the general formula,

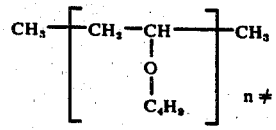

and a mol.wt. of 9000–10,000 ... 3.0
and as fat-soluble anthraquinone green stain or dye, 1,4-bis- (p-toluidino)-anthraquinone... 0.02

The adhesive was prepared as follows. 387.8grams of 2-ethoxyethyl-α-cyanoacrylate were loaded into a flask provided with a mechanical stirrer in an atmosphere of dry nitrogen. Then, 12 grams of the polyvinyl-n-butyl ether was added in drops with constant stirring and 0.08 grams of the fat-soluble dye 1,4-bis-(p-toluidino)-anthraquinone, dried to constant weight was added.

Stirring is discontinued as soon as the mass becomes homogeneous.

The adhesive is filled into ampoules as described in Example 1.

EXAMPLE 3

A medical adhesive having the following composition in percent by weight was prepared.
2-ethoxy-α-cyanoacrylate ... 84.9
polyvinyl-n-butyl ether, having the general formula,

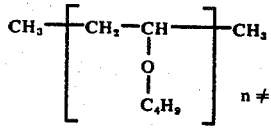

and a mol.wt. of 4,000–10,000 ... 15
and as fat-soluble anthraquinone green stain or dye, 1,4-bis-(p-toluidino)-anthraquinone ... 0.1

The procedure for preparing the adhesive was the same as described in Example 2. As the adhesive was filled into the ampoules, it was periodically stirred to prevent delamination. The adhesive should be shaken before use.

As mentioned above, the medical adhesive of thin invention has many advantages and can be used to join various soft tissues in surgical operations. Depending on the size of the operative wound, the adhesive can be used alone or in combination with suturing or autohomotransplantation.

In addition to the specific uses mentioned above, the adhesive of this invention can be used in the following cases such as in surgery of the respiratory organs for additional or extra fixation of the broncheal stump after manual or mechanical suturing, for closing the wound of the pulmonary parenchyma (alone or in combination with pleural grafting), for extra hermetization and fastening of anastomosis of the tracheobroncheal tree, for closing insufficiency of the broncheal stump and fistula; in cardiovascular surgery for sealing sutures on the heart and related vessels in operations with extracorporeal circulation of blood and also for stopping parenchymatous hemorrhage associated with heparin administration; in surgery of the extrahepatic bile ducts and liver such as for closing wound surfaces on the liver and for sealing sutures on the bile ducts; in operative urology for closing the wound after resection of the renal pole, for closing nephrotic section on the pelvis, for closing cuts on the ureter and for sealing sutures on bladder wounds; and in addition, in surgery of the alimentary organs for extra sealing and fastening of inter-intestine, esophagogastric, esophagointestinal and other anastomoses; in ophthalmology for closing wounds on the cornea and in stepped transplantation of the cornea; and in neurosurgery for closing wounds on the hard, cerebra membrane.

Numerous other advantages and uses of the medical adhesive of this invention will be readily apparent to those skilled in the art. Therefore, it is to be understood that numerous variations of the disclosed embodiments of this invention can be made without departing from the spirit and scope thereof and accordingly, this invention is not to be limited to the embodiments disclosed herein except as defined in the appended claims.

What is claimed is:

1. A medical adhesive composition comprising a major proportion of 2-ethoxyethyl-α-cyanoacrylate and minor proportions of polyvinyl-n-butyl ether having the general formula,

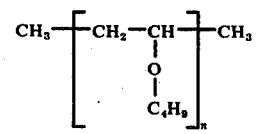

and having a molecular weight in a range of about 4,000 to about 10,000 and wherein $n$ has a value sufficient to give a molecular weight in the recited range and as a fat-soluble, green anthraquinone dye 1,4-bis-(p-toluidino)-anthraquinone having the formula,

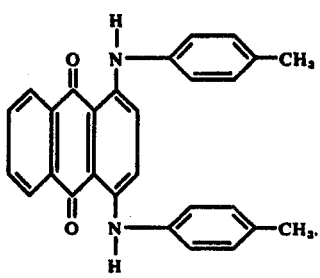

2. A medical adhesive composition comprising the following components in percent by weight:
2-ethoxyethyl-α-cyanoacrylate . . . 84.9–96.98
polyvinyl-n-butyl ether having the general formula,

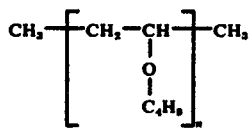

having a molecular weight in a range of from about 4,000 to about 10,000 3–15
and as a fat-soluble, green anthraquinone dye, 1,4-bis-(p-toluidino)-anthraquinone having the formula,

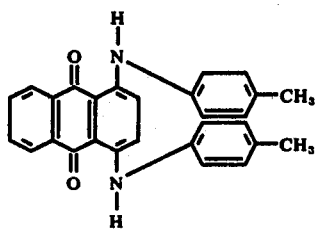

3. A medical adhesive composition according to claim 2 comprising the following quantities of components in percent by weight: 94.15 percent percent of the cyanoacrylate, 5.8 percent of the polyvinyl-n-butyl ether having a molecular weight from about 7,000 to and 8,000 0.05 of the 1,4-bis-(p-toluidinol- anthraquinone dye.

* * * * *